United States Patent [19]

Hammesfahr et al.

[11] Patent Number: 4,867,682

[45] Date of Patent: Sep. 19, 1989

[54] DENTAL IMPRESSION TRAY

[75] Inventors: Paul D. Hammesfahr, Dover; Steven R. Jefferies, Milford, both of Del.; Ronald L. Sitzema, Jr., Ellsworth, Mich.

[73] Assignee: Dentsply Research & Development Corp., Milford, Del.

[21] Appl. No.: 120,304

[22] Filed: Nov. 13, 1987

[51] Int. Cl.$^4$ ................................................. A61C 9/00
[52] U.S. Cl. ........................................ 433/37; 433/229
[58] Field of Search .................... 433/37, 40, 29, 149, 433/229

[56] References Cited

U.S. PATENT DOCUMENTS

| | | | |
|---|---|---|---|
| 3,882,601 | 5/1975 | Jahn | 433/214 |
| 4,267,133 | 5/1981 | Kohmura et al. | 433/199 |
| 4,411,625 | 10/1983 | Koblitz et al. | 433/217 |
| 4,449,928 | 5/1984 | von Weissenfluh | 433/40 |
| 4,468,202 | 8/1984 | Cohen | 433/199 |
| 4,521,193 | 6/1985 | Cialone | 433/199 |
| 4,543,063 | 9/1985 | Cohen | 433/175 |
| 4,544,359 | 10/1985 | Waknine | 523/115 |
| 4,544,467 | 10/1985 | Bunker et al. | 204/159.24 |
| 4,553,936 | 11/1985 | Wang | 433/37 |
| 4,631,030 | 12/1986 | von Weissenfluh | 433/149 |

Primary Examiner—John J. Wilson
Attorney, Agent, or Firm—Edward J. Hanson, Jr.; David E. Wheeler

[57] ABSTRACT

A dental impression tray and method of using it to form in a light-polymerizable impression material an impression of a portion of dental anatomy in an oral cavity, the tray being formed of transparent material, preferably clear plastic, and molded into a channel-like shape defined by walls capable of having visible actinic light applied to the walls transmitted both through and within the walls. At least some of the outer edge portions of the tray are beveled, guiding light that has entered the walls of the tray against exiting loss that would not be effective in initiating polymerization of the impression material.

9 Claims, 3 Drawing Sheets

DENTAL IMPRESSION TRAY

BACKGROUND OF THE INVENTION

This invention pertains to a dental impression tray and a method of using the same to effect maximum curing by polymerization of impression material to form a negative impression of at least a part of dental anatomy in an oral cavity, the polymerization being preferably effected by visible actinic light rays applied to the tray and impression material therein while the tray and impression material are held firmly pressed against the dental anatomy which is to be reproduced in the form of a model or otherwise.

In general, for many years, it has been common practice in dentistry to form a model or cast of dental anatomy in the oral cavity of a patient by utilizing a suitable size and shape of a dental impression tray into which a predetermined amount of settable impression material is placed for manual impressment against the anatomy, such as a full or partial gum, with or without teeth. Normally, an appreciable amount of time is required to effect, by currently used activators and otherwise, suitable curing of presently available impression material into an elastomeric form having permanent memory. This technique necessarily monopolizes the full time of a dentist or assistant for the required period of curing time and during which, no other activities can be undertaken by the dentist or assistant.

Dental impression trays have been used for many years to contain pastes, for example, during the taking of an impression of oral tissues or dental anatomy. Usually these trays are of metal and exist in a variety of shapes and sizes suitable for various situations. In recent years plastics have been substituted for metal, particularly for single use so as to be disposable. Some of these trays have been fitted with coolant systems for hardening pastes into gels but, in most instances, the viscous pastes are converted to elastic or rubbery condition by a reaction initiated by the mixing of two components immediately before the material is placed in the tray.

There is a published patent, U.S. Pat. No. 4,553,936, showing a tray for light curing wherein all of the surfaces of the tray are not light transparent.

One problem with existing impression trays and taking impressions is that a significant amount of the mouth area is being covered by a large object for a long period of time--up to fifteen minutes, for example. The natural human reflex action in this situation is to gag, resulting in changing the contours of some of the tissue and musculature which was to be reproduced while static. Also, with the passage of several minutes times, salivation occurs from glands located near the impression area and these fluids affect the quality of impression reproduction.

A recent dental development has occurred in the area of restoratives and sealants where actinic radiation has been used in conjunction with photosensitive accelerators to initiate prompt and rapid polymerization precisely when the dentist is ready with the patient. In so far as is known there have been no successful significant commercial availability of this technology in applicability to large area elastomer curing or to materials needing to be confined in a radiation-conducting vehicle.

After years of research the present invention has been conceived and reduced to practice by devising a new and improved novel type of impression tray with which harmless visible actinic light is used to effect curing the material by polymerizing impression material. A suitable polymeric elastomer forming material for practicing the invention is also shown in U.S. Pat. No. 4,553,936 and U.S. patent application Ser. No. 032,903 filed March 31, 1987, both assigned to the same assignee as the present application, the contents of which are incorporated herein by reference. Additional materials are shown in a companion patent application U.S. Ser. No. 120,269 filed Nov. 13, 1987, and assigned to the same assignee as the instant invention, the contents of which are incorporated herein by reference.

SUMMARY OF THE INVENTION

By an aspect of the invention a new dental impression tray is provided for use with dental impression material capable of being polymerized by exposure to actinic light, especially actinic light in the visible light spectrum. The dental tray has a channel-shaped cross-section providing a recess adapted to hold a predetermined amount of dental impression material for forming the impression of opposite surfaces of teeth therein. The tray has a substantially planar wall that forms the bottom of the channel and at least a first projecting wall projecting from one side of the bottom wall. The projecting wall projects from the bottom wall at an angle of about 70° to about 120°. The tray is formed from material that is substantially transparent. The improvement includes merging the bottom wall and the projecting wall at a joint wall which has an effective outside angle of about 35° to about 55° to both the bottom wall and the projecting wall. The joint wall predominately transmitting actinic light and the side wall and the bottom wall capable of both substantial passing and substantial transmitting of actinic light. By another aspect the invention involves a method of forming a dental impression in polymerizable flowable dental impression material capable of being rendered permanently elastomeric upon polymerization using actinic light and forming a mold comprising the steps of;

a. placing a predetermined quantity of flowable dental impression material in a transparent impression tray having walls defining a recess. The walls having faces that will be outwardly exposed when the tray is in use and faces that are impression material contacting, b. impressing the material in the tray against dental anatomy in an oral cavity of which a mold is desired, c. applying visible actinic light to substantially the majority of the outwardly exposed wall face area of the tray and d. passing a substantial part of the visible actinic light directly through the walls of the tray and directly through the impression material contacting wall faces of the tray and transmitting and reflecting a substantial part of the visible actinic light within the walls of the tray and passing a substantial portion of the transmitted and reflected light through the impression material contacting wall faces of the tray insuring a substantially thorough penetration of the material by the visible actinic light.

DETAILED DESCRIPTION OF THE PREFERRED EMBODIMENT OF THE INVENTION

The present invention is concerned with dental trays for use with dental impression material capable of being polymerized by exposure to actinic light. The dental impression tray is preferably curved sufficient to receive at least a partial arch-shaped group of teeth and channel-shaped in cross-section and wider than the teeth to be received therein. The channel-shaped cross-section provides a recess adapted to hold an approximate predetermined amount of the dental impression material for forming the impression of opposite surfaces of teeth therein.

The present invention has several important aspects. A first aspect is the provision of a dental impression tray made of light transparent material molded into a dental tray configuration that is similar in shape to conventional metallic impression trays but having joint walls joining the tray's bottom and side walls such that light within the walls is retained against undesirable exit at the junctures while the admittance of new light is at all times facilitated.

A second aspect of the invention comprises utilizing plastic having special optical properties that enhance the passage of the light to the light-polymerizable impression material which is held in contact with a desired portion of dental anatomy within an oral cavity and contained within the tray.

A third aspect of the invention is the provisions of a method for making dental impressions that enhances and maximizes the polymerization of the material in the shortest possible time to a degree of integrity.

Looking now at FIGS. 1-3 and 3(a), it is to be understood that the substantially U shaped transparent dental tray is exemplary. The tray 10 illustrated is specifically intended for preferably taking the lower full arch of teeth within the oral cavity of a dental patient. It will be understood that the tray after being filled is inverted to the relative position illustrated in FIGS. 1-3 with the bottom wall 11 of the channel or recess 9 being disposed above the teeth as illustrated in FIG. 4.

Looking again at FIGS. 1-3 and 3(a), projecting side walls 12 and 13 respectively extend from opposite sides of the bottom wall 11 and are joined with the bridging or bottom wall 11 by joint or bevel walls 14 and 15 respectively to form the U shaped recess. The projecting walls 12 and 13 project away from the bottom wall at an angle of approximately 90° and the joint walls have respective definitive outside angles of 45° from both the bottom wall 11 and from the respective projecting walls 12 and 13. Preferably the projecting walls extend from the bottom wall at respective angles of 70° to 120°, more preferably 80° to 110° and most preferably 85° to 95°. The projecting walls are curved as they form the arch of the tray to accommodate the arch of the teeth but strait in vertical or projecting extent so as to in effect offer a curving planar surface for direct impingement and passing through of light. The dominant direction of lay for the bottom wall 11 is represented by phantom line a and the dominant direction of projection of projecting wall 13 is represented by phantom line b which have an angle of interception of 90°.

Figures 1, 2, 3:
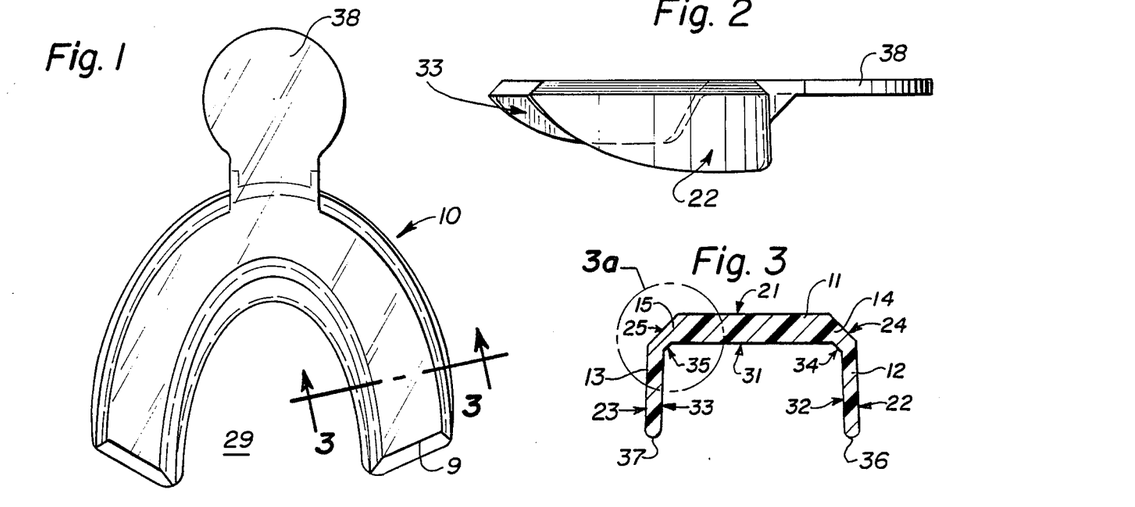
FIG. 1 is a plan view of one embodiment of the impression tray of the present invention for taking the full lower arch of dentition.
FIG. 2 is a side elevational view of the tray shown in FIG. 1.
FIG. 3 is a cross-sectional view taken on line 3—3 of FIG. 1.

Preferably the joint walls are disposed with their outer surface or definitive and effective outside angle to the projecting walls and the bottom walls of 35° to 55° (125° to 145°), more preferably 40° to 50° (130° to 140°) and most preferably 43° to 47° (133° to 137°). The dominant direction of lay or disposition of the joint walls is represented by phantom line c which has an angle of interception with the bottom walls dominant lay a of 45° or 135° depending on the direction from which it is measured. The identical angles apply to the lay b of the projecting wall but is not illustrated to avoid in the drawing clutter. The joint walls at the inside of the tray within the U or channel may have substantially no dimension or width or a slight dimension as illustrated in FIG. 3 at 34 and 35.

Figure 4:
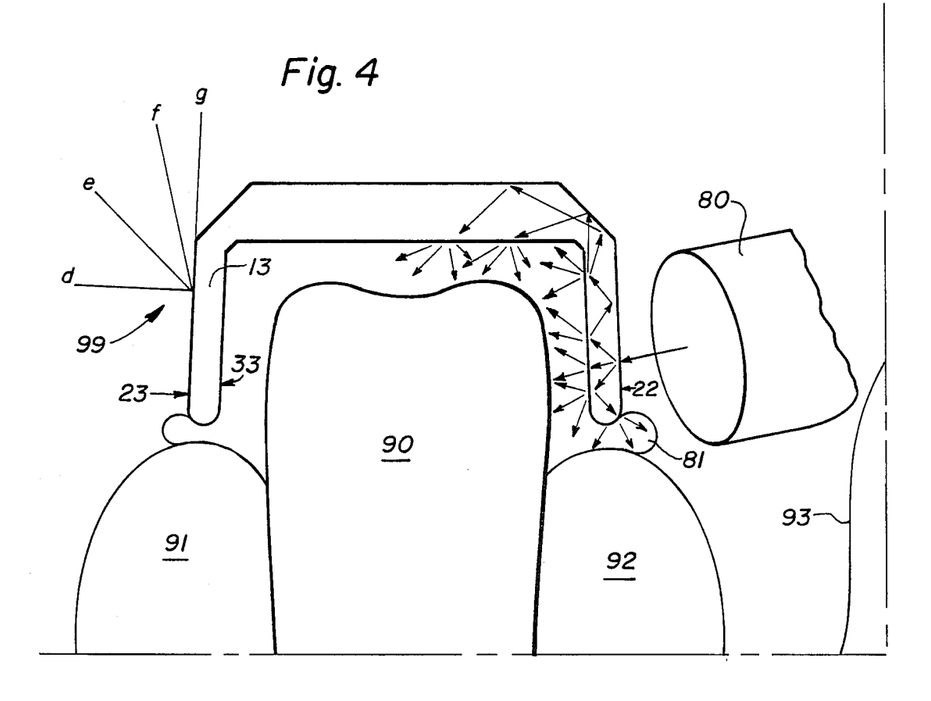
FIG. 4 is an enlarged schematic of the view of FIG. 3 with the tray in operation.

The walls 11, 12, 13, 14, and 15 have respective faces 21, 22, 23, 24 and 25 that are outwardly exposed to receive the impingement of light as shown in FIG. 4. Other faces of the walls 11, 12, 13, 14 and 15 are impression material contacting faces, respectively 31, 32, 33, 34 and 35. The outer face edges 36 and 37 would usually be within the definition of faces that are impression material contacting during tray use as illustrated in FIG. 4. A handle 38 is provided for the convenient gripping of the tray for its placement in a patients mouth by a dental professional.

Figure 5:
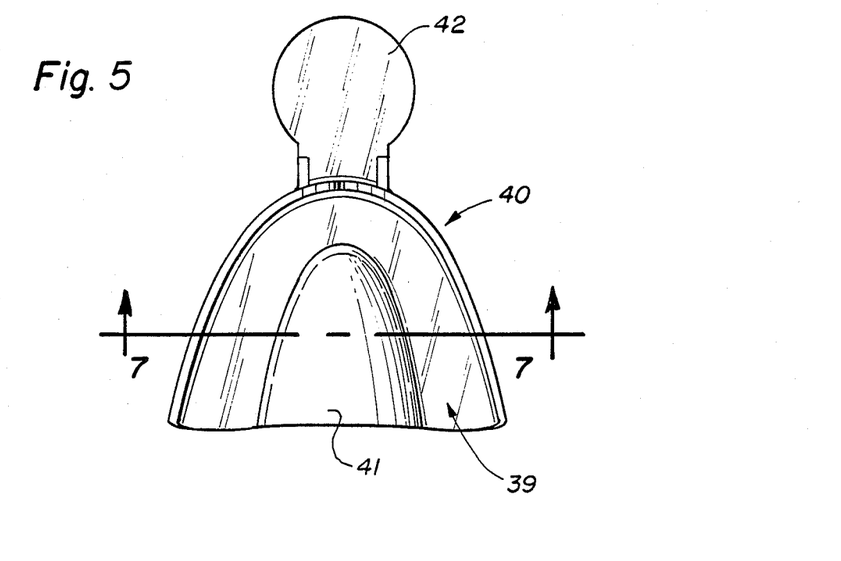
FIG. 5 is a plan view of another embodiment of the impression tray of the present invention for taking the full upper arch of dentition.
Figure 6:
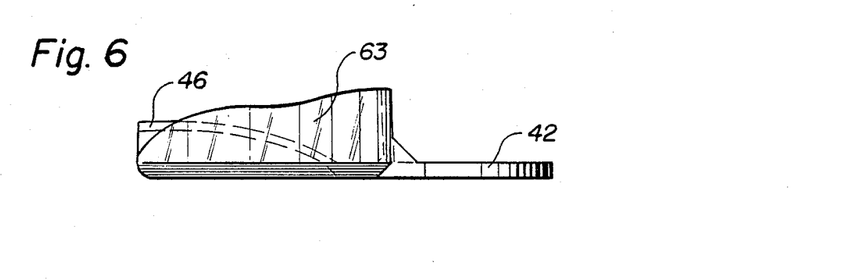
FIG. 6 is a side elevation of the tray shown in FIG. 5.
Figure 7:
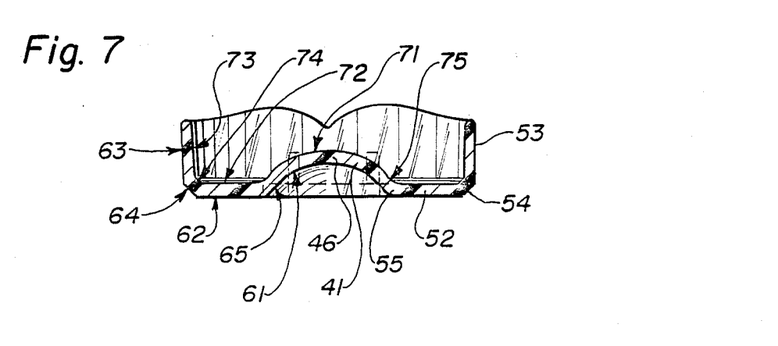
FIG. 7 is a sectional view taken on the line 7—7 of FIG. 5.

Looking next at FIGS. 5-7 an alternate specie of the dental impression tray 40 may be seen. Alternate tray 40 is made of transparent material and is conformed to a general U shaped channel or recess 39 for taking a complete impression of an upper arch of teeth where it is not necessary to accommodate the tongue (in the space 29 of tray 10) but instead a palate plate wall 41 is provided to push the dental impression material in the conventional manner against the inside of the upper teeth and toward the roof of the mouth. Dental impression tray 40 also has a handle member 42 for gripping by the dental professional to aid in positioning the tray 40 within the dental patients mouth or oral cavity. Tray 40 has a bottom wall 52, a projecting wall 53 and palate wall 41 as seen in FIG. 7. The bottom wall 52 is joined to the projecting wall 53 by the joint wall 54. The preferred angles of relation between the walls in tray 40 are the same as that previously recited with regard to the tray 10 and the required principles of operation are the same.

It may be seen that the palate wall 41 joins with the bottom wall 52 at a joint wall 55. It is important that the joint wall or juncture area 55 join with the bottom wall 52 at the angle previously set forth with regard to the relationship of the joint wall 54 and the bottom wall 52. However, in the case of the palate wall 41 the joint wall may merge directly into and be part of the palate wall 41 which may then slowly diminish in angle to the dimension of a 0° angle from the bottom wall 52 at its apex 46, or that is parallel with the bottom wall.

Figures 3A, 8, 9:
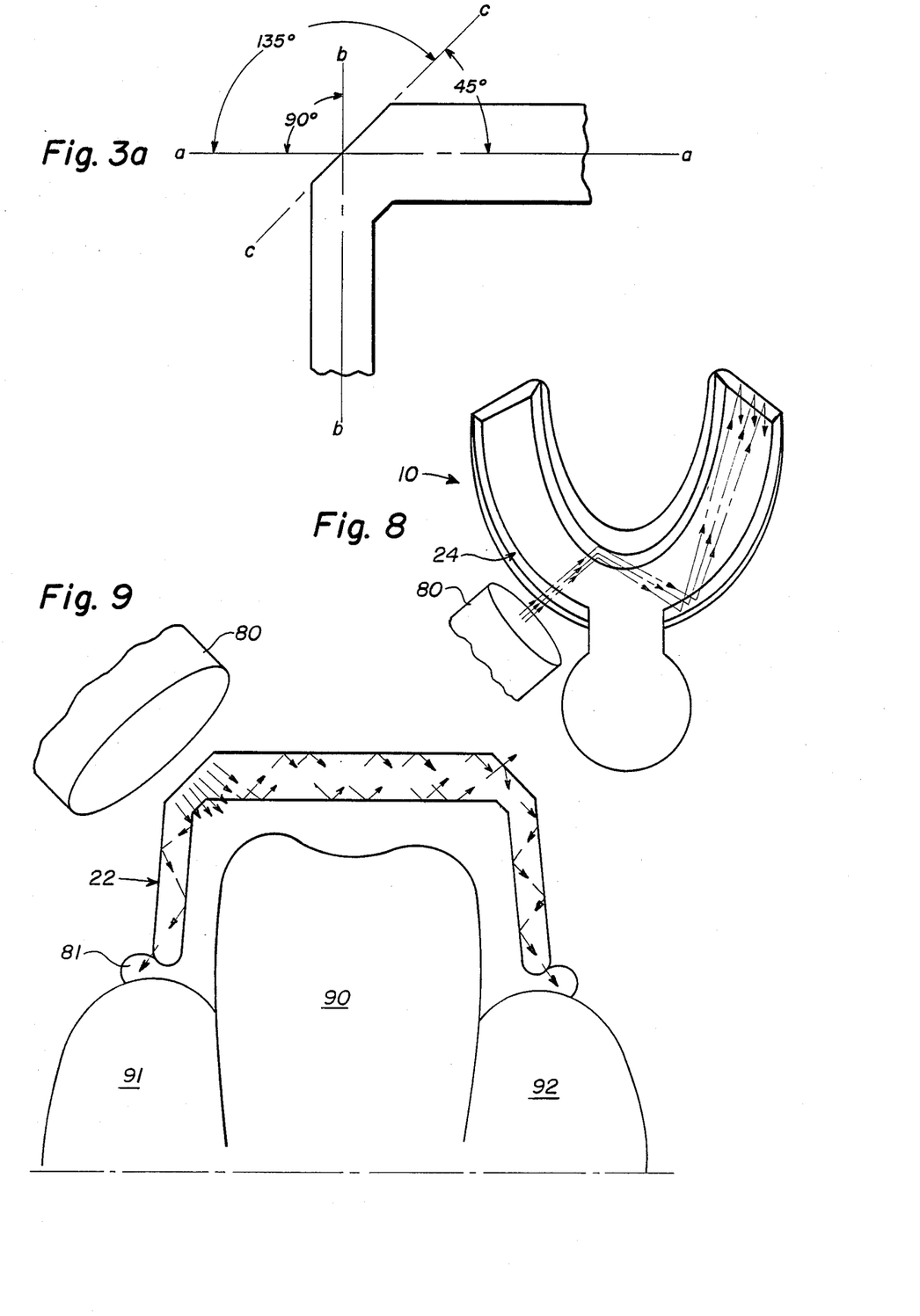
FIG. 3(a) is an enlarged schematic of breakaway 3(a) of FIG. 3 illustrating angular relationships.
FIG. 8 is a schematic of the tray of FIG. 1 illustrating the path of certain light transmitted into the tray.
FIG. 9 is an enlarged schematic similar to FIG. 4 but with the light applied to a different area.

FIG. 8 illustrates light applied against a joint wall and then reflecting off of wall faces as it is optically transmitted within the tray wall.

The transparent clear plastic materials from which the tray of the present invention is constructed is an important aspect of the preferred embodiments of the invention. The tray is preferably made by standard injection molding procedure from resins having the desired properties of superior passing and transmission of visible light. The preferred resins are the acrylates, styrenes, and polycarbonates and the less preferred polysulfones. Especially preferred are the acrylic. While the walls of the tray are preferable completely transparent, areas of decoration and the like that are not transparent could be present.

The plastic when formed into the tray should preferably transmit at least 50%, more preferably at least 70% and most preferably at least 80% of the light from at least two different wave lengths within the visible actinic light spectrum of 350 to 600 nanometers, that are spaced at least 10 nanometers apart. For example, the 360 to 370 nanometer wave lengths. Percent light transmission is measured according to the test of ASTM D-1003 Light Transmittance and Haze (1976).

To illustrate how some light rays pass directly through the tray walls and others are transmitted and reflected within the walls of the tray attention is called to FIG. 4. As the arrows depict, the light that enters the tray walls at an angle tends to be refracted and reflected to other angles and to be transported inside the walls of the tray until an angle is attained that is sufficiently direct or approximating a 0° angle to a face or surface of a wall to allow exit from the wall and in the case of the inside tray walls entrance into the impression material contacting the tray walls. Of course, some of the transmitted and reflected light exits the tray and is wasted or lost.

The optics of the dental impression tray will now be more fully explained as they are believed to be understood. Looking at the area of FIG. 4 designated as 99 various light impingement angles are illustrated. Line represents light impinging straight on to face 23 and in this patent application this is designated as a light angle of 0°. Line e is 42.2° from line d and this is at the substantial angle differentiating the passage of light through the face 23 and the reflection or refraction of the light which shall be called the "r factor" when the angle of impingement exceeds this 42.2° angle. Thus if light impinges or strikes face 23 at the angle of 75° represented by line f it will not enter the wall through the face 23 to a substantial extent or in other words most of the light will be reflected or refracted away. Some small amount of light scatter may occur but not enough to provide effective energy levels at present operable or practically achievable light output levels. Thus as the angle of light is smaller than 42.2° or closer to the 0° or straight on incidence in its impingement on face 23 it will pass substantially through the face into the wall 13. As the angle of light is greater than 42.2° or closer to 90° from the 0°, the light will be substantially reflected or refracted and not pass into the wall through the face. Line g is at 90° from line d.

The principle is exactly the same with respect to light passing through face 33 to exit the wall. If the angle of incidence is less than 42.2° the light will substantially exit through the face 33 from the wall 13 and if the angle of incidence is greater than 42.2° reflection and refraction within the wall 13 will retain the light substantially within the wall until the light incidence or impingement angle with a wall face reaches less than 42.2° as is diagrammatically illustrated in FIGS. 4 and 9 by the small diagrammatic arrows depicting light movement, whereupon the light will substantially exit the wall.

To minimize the refraction the opposed surfaces of a tray wall, such as surfaces 23 and 33 of wall 13 should be essentially or substantially parallel to one another and this is preferred. However, it is necessary that the side walls 12 and 13 curve to conform to the inside curve of dentition within a patients mouth. By curving them together in parallel refraction and reflection can be reduced but not eliminated. The plastic wall itself also probably significantly bends the light as the light passes through.

The joint walls 14 and 15 of FIG. 3 do not pass the predominant portion of their light into the impression material but act as an entrance way for the light to pipe into the respective side walls 12 and 13 and assist in the cure of the material at the gum line. Its disadvantage is that it does not allow the majority of that light to pass directly into the corner of the impression material. This disadvantage is more than made up for by serving to direct the light that has been scattered, or entered the wall at an angle, and been refracted or reflected within the bottom wall and projecting or side walls in a manner causing a substantial portion to eventually exit into the dental impression material. Except for this critical construction employing the joint wall, much of the light would exit and be lost at the wall junctures.

Because of the depth of the impression material frequently required to enter into the deeper anatomical areas that are to have impressions taken, it is important in the usual instance to have a light output of at least 10,000 foot candles more preferably at least 12,000 foot candles and most preferably at least 14,500 foot candles. Foot candle is measured by putting a photo cell (UDT Model 263 using 151 diffusion plate having a diameter of 0.8 inch) directly against light output (pipe of PRISMETICS ® light) and measure with photometer (UDT) and read in foot candles. It is also preferable that the light output be between 300–1000 milliwatts/cm$^2$, more preferably 400–800, and most preferably 500–700 milliwatts/cm$^2$. A preferred light for use with the present invention is the PRISMETICS ® light available from Dentsply International Inc. Foot candles is determined by taking readings using a spectroradometer and relating these to a National Bureau of Standard traceable source.

By the present invention in another aspect a method is provided for forming a dental impression from polymerizable flowable impression material capable of being rendered a permanently elastomeric solid by photopolymerization with actinic light, preferably in the visible light spectrum. The method involves placing a predetermined quantity of the impression material 81 sufficient to form the intended molded shape into a transparent impression tray such as the ones previously described. The mold of the dentition is then formed in the recess of the tray defined by the channel walls. The walls have faces that will be outwardly exposed when the tray is in use as shown in FIGS. 4 and 9. In the instance of tray 10 as shown in FIG. 3 this would be at faces 21, 22, 23, 24 and 25. The cheek 93 can be pushed aside to expose face 22 to the light 80 and the tongue can be pushed aside to expose face 23 to the light 80 which would be moved to an appropriate position in the obvious manner. The inside faces 31, 32, 33, 34 and 35 of the tray will be engaged with the impression material in use and are impression material contacting faces as previously described.

The dental practitioner taking the dental impression, places the filled tray in the dental patients mouth and forces the tray against the dental anatomy by pressing upon the tray. In this manner the area of the dental anatomy that is to have its mold formed is encompassed by the flowable dental impression material which is impressed upon it. As shown in FIGS. 4 and 9, the dental impression material is forced over the tooth 90 and against the gum tissue at 91 and 92. Then actinic light is applied to substantially the majority of the outwardly exposed wall faces of the tray which are the faces previously described above.

The actinic light is applied in a manner that passes a substantial part of the light directly through the walls of the tray. This is in particular accomplished in part by aligning the light so a substantial portion of the light rays strike the outer exposed face of the tray at substantially a 0° angle with the alignment extending to a substantially 0° angle to the faces of the tray that are in contact with the impression material to facilitate the light rays penetration directly through the walls without being reflected or refracted at an angle at the exit face of a tray wall, such as the faces in contact with the impression material. This facilitates the light rays passing directly through the impression material contacting wall faces of the tray. An additional and often substantial portion of the light enters the tray at the "r factor" angle to the exiting face of a wall causing the transmitting and reflecting of this part of the visible actinic light within the walls of the tray until it strikes a face of the tray at an angle less than the "r factor" allowing the light's exit. Some of the light will exit at the inside face of the tray and enter the impression material, and together with the directly passed light, serve to assure or insure a thorough penetration of at least substantially all of the impression material by the visible actinic light thereby bring about sufficient polymerization to render the dental impression material a permanently elastomeric mold of the dental anatomy. A substantial portion of the actinic light is passed directly to the dental impression material nd a substantial portion is in the form of transmitted and reflected light of which a substantial portion passes through the impression material contacting wall faces of the tray.

The joint wall does not pass the predominant portion of the light it receives as previously described because there is a very limited amount of impression material contacting wall face relative to outwardly exposed face. The joint wall is, in effect, a built-in optic. By providing the joint wall or prism wall, light applied thereto can be utilized to assure good coverage of all of the impression material with impinging light and also to help reduce light being lost. The operation of this feature has already been explained. By providing a substantially planar bottom wall with parallel faces a substantial portion of the light can be applied to the bottom wall substantially at a direct 0° angle allowing passing of a substantial portion of the light directly through the wall to the impression material. The projecting walls within the preferred angles preferably also have what in effect are curving planar walls having substantially parallel faces providing for a substantial portion of the light applied to the side walls to be applied at a direct 0° angle allowing passing of a substantial portion of the light directly through the wall to the impression material.

Other lights can also be used, for instance a light that fits over substantially the entire outside surfaces of the tray so as to simultaneously light up all of the walls at the same time. In addition, more than one PRISMETICS ® light can be used at the same time.

Preferably the impression material should be cured within the tray to a degree of integrity allowing its removal within 7 minutes more preferably 5 minutes and most 3 minutes or less.

An example preferred visible light curable impression material of the preferred polyether urethane dimethacrylate type is prepared as follows:

| | |
|---|---|
| Voranol 2120 (polypropylene glycol) (MW 2000) | 68.25% |
| TMDI (Trimethylhexamethylene diisocyanate) | 14.34% |
| Stannous Octoate | 0.05% |
| HEMA (Hydroxyethyl methacrylate) | 3.14% |
| 1,4-Butanediol | 4.29% |
| TIM (Reaction product of TMDI and HEMA) | 8.10% |
| HEMA | 1.82% |
| Phosphoric Acid - Water Solution (1:1) | 0.0021% |

The polypropylene glycol (Voranol 2120) with an average molecular weight of 2000 is first mixed with the phosphoric acid solution to neutralize residual base in the polypropylene glycol. Then the stannous octoate is added as the catalyst for urethane formation. A 2/1 excess of TMDI is added to form an isocyanate terminated prepolymer. Then part of the residual isocyanate is capped with HEMA. The remainder is chain extended with 1,4-Butanediol. Then TIM is added. TIM is the reaction product of 1 mole (2 equivalents) of TMDI and 1 mole (1 equivalent) of HEMA. It has one free isocyanate end and one methacrylate end when the reaction is complete. The isocyanate portion reacts with the remaining hydroxyl group from 1,4-Butanediol. Finally, a small amount of HEMA is added to react any residual isocyanate.

A comparison of moles and equivalents of the ingredients is seen below:

| | Moles | Equivalents |
|---|---|---|
| Voranol 2120 | 1 | 2 |
| TMDI | 2 | 4 |
| HEMA | 0.7 | 0.7 |
| 1,4-Butanediol | 1.4 | 2.8 |
| TIM | 0.7 | 0.7 |
| HEMA | 0.4 | 0.4 |

| Activated Resin | |
|---|---|
| Resin described above | 98.78% |
| Camphorquinone | 0.20% |
| 4-Dimethylaminobenzonitrile | 0.92% |
| Butylated Hydroxy Toluene (BHT) | 0.10% |

| Heavy Body Tray Material | |
|---|---|
| Activated Resin described above | 45.95% |
| Fused Quartz (average particle size 15-25 microns) | 42.37% |
| Aerosil R-972 fumed silica | 9.04% |
| Dayglo A-21 Corona Magenta pigment | 0.0824% |

-continued

Heavy Body Tray Material

| | |
|---|---|
| Palatinol 711P (Di-C$_{7-9-11}$) Alkyl Phthalate | 2.00% |
| Ken React LICA 09 | 0.05% |
| Gamma-Methacryloxypropyltrimethoxysilane | 0.50% |

Light Body Syringeable Material

| | |
|---|---|
| Activated resin described previously | 54.76% |
| Fused Quartz (average particle size 15-25 microns) | 39.68% |
| Aerosil R-972 fumed silica | 1.55% |
| Dayglo A-19 Horizon Blue pigment | 0.25% |
| Palatinol 711P (Di-C$_{7-9-11}$) Alkyl Phthalate | 3.10% |
| Ken React LICA 09 | 0.13% |
| Gamma Methacryloxpropyltrimethoxysilane | 0.52% |

The material described above has the advantages of unlimited work time, no mixing, command cure, and a fast cure. Furthermore, the impression has good readability, is hydrophilic, and can be poured up immediately in gypsum or epoxy.

In a preferred embodiment, peppermint may be added to the heavy body material.

The trays of the present invention are preferably used only once and in use a tray adhesive is used to bind the dental impression material to the dental impression tray acting as a tie layer. The preferred resins for making the dental impression tray are the acrylic resins as previously stated and the preferred adhesives will have a solvent effect on the surface of the tray to provide a superior bond with the tray. An example preferred visible light curable adhesive is prepared as follows:

An adhesive for use in the invention, which is painted on the dental trays before the trays are filled with VLC Impression Material, is prepared according to the following example:

Adhesive Preparation

Preparation of BIM ( the reaction product of Bis-GMA and IEM, needed for the preparation TNCO, the reaction product of Bis-GMA and TMDI).

The following ingredients were used:
626.0 g (1.218 moles) of 2,2-Bis[4-3 (3-methacryloxy-2-hydroxypropoxy-phenyl]-propane (Bis-GMA)
234.4 g (0.808 moles) of Triethyleneglycol dimethacrylate (TEGDMA)
234.4 g (0.923 moles) of 1,6 Hexanediol dimethacrylate (HMDMA)
321.5 g (2.074 moles) of Isocyanatoethyl methacrylate (IEM)
1.40 g (0.003 moles) of Stannous Ocotate (T-9)
1.12 g (0.0051 moles) of Butylated Hydroxy Toluene (BHT)

The Bis-GMA was weighed into a dry 2 liter reactor. The TEGDMA and HMDMA were added to the Bis-GMA. Stirring and dry air flow through the reactor was begun and the mixture was stirred for 30 minutes until it was homogenous. Then the stannous octoate was added dropwise and stirred in for 15 minutes. The IEM was weighed into a beaker and poured into a 500 ml. addition funnel where it was added dropwise to the reactor. The addition was done at a speed to keep the reactor temperature below 50° C. Addition took approximately 3½ hours. It was allowed to stir overnight. The next morning a sample was taken, found to be free of residual IEM, and was unloaded from the reactor.

Preparation of TNCO

The following materials were used:
541.5 g (1.05 moles) of 2,2-Bis[4-3(3-methacryloxy-2-hydroxypropoxy)-phenyl]propane (Bis-GMA)
541.5 g (0.848 moles) of BIM resin
111.8 g (0.386 moles) of TEGDMA
111.8 g (0.440 moles) of HMDMA
190.4 g (0.907 moles) of Trimethylhexamethylene Diisocyanate (TMDI)
2.25 g (0.0048 moles) of T-9
1.20 g (0.0055 moles) of BHT The Bis-GMA and BIM were weighed into a dry 2 liter reactor. TEGDMA and HMDMA are when weighed into the reactor. Stirring and dry air flow through the reactor were begun. The reactor contents were stirred for 30 minutes until a homogenous mixture resulted. The T-9 was then added to the reactor dropwise and mixed in 15 minutes. Then the TMDI was weighed into a beaker and poured into a 250 ml. addition funnel where it was added dropwise. Addition was done at a speed to keep the temperature below 50° C. Addition was complete in approximately 1½ hours. The resin was stirred for 36 hours maintaining the temperature between 45°-53° C. Then a sample was taken, found to be free of residual TMDI, and the reactor was unloaded.

Initiation of TNCO Resin

The TNCO resin was initiated for a visible light curing system as outlined below:

| | |
|---|---|
| TNCO resin | 99.24% |
| Camphorquinone | 0.15% |
| 4-Dimethylaminobenzonitrile | 0.61% |

Procedurally, the TNCO resin was weighed into a glass jar. The Camphorquinone and 4-Dimethylaminobenzonitrile were weighed out separately and added to the TNCO. This mixture was heated to 50° C. using a water bath and then stirred for 30-45 minutes until it was homogenous.

Preparation of Adhesive

The following ingredients were used:

| | |
|---|---|
| Iniated TNCO resin | 56.71% |
| Methylene Chloride | 23.81% |
| Nitromethane | 19.48% |

Procedure:

The warm initiated TNCO resin was weighed into a beaker. The nitromethane and methylene chloride were weighed into a glass jar and stirred for 2-3 minutes. Then the warmed TNCO resin was slowly poured into the methylene cloride/nitromethane mixture with stirring. The mixture was stirred after addition was complete for 20 minutes.

The invention is further illustrated by the following example.

EXAMPLE 1

A dental impression tray as shown in FIGS. 1-3 was injection molded using a polyacrylic (Rohm and Haus, Plexiglas VO-52, UVA 1). The material is classified as colorless and exhibits the following properties: At a wave length of 350 nanometers, this material transmits 80% of that light spectrum. At 360 nanometers it transmits approximately 85% of that light spectrum and at 370 nanometers it transmits 90% of that light spectrum up to and including 600 nanometers. The material has a specific gravity of 1.19, an optical refractive index of 1.49, a light transmission value of 91% in the thickness of 0.100, and exhibits approximately 2% haze. This acrylic material exhibits very low water absorption and excellent resistance to chemicals used in the curing of the impression material.

A dental patient was prepared in conventional manner by using cord to retract the gingiva and generally cleaning and drying the area to have its impression taken.

The dental impression tray was coated on its inside faces with the dental tray adhesive described above using a stiff bristle brush to provide a complete and substantially uninterrupted film. This was determined by visual inspection. The methylene chloride/nitromethane solvent blend slightly dissolved the surface of the polyacrylic tray carrying the urethane resin with it. Residual solvent was evaporated with an air stream.

About 22 ml of the heavy body tray material described above was loaded into the dental impression tray. The light body syringable material described above was syringed thinly around the teeth and against the gums in conventional manner on a full set of lower teeth. Then the previously filled tray was engaged on the full set of lower arch teeth in the patients mouth by hand in conventional manner. While holding the tray firmly in place with one hand a PRISMETICS ® Lite with a 10 mm diameter fiber optic probe was aimed substantially directly on all of the exposed areas of the faces of the tray. By the light being aimed substantially directly at the exposed face areas it is meant with an angle of approximately 0°±20°. While the light is shown in FIG. 9 spaced from contact with the face 25 (FIG. 3) of the bevel or joint wall, it is preferable and in fact was at least part of the time, brought into direct contact with the face 25. The light was substantially continuously moved and the entire exposure time to form a superior dental impression mold was about 1.5 to 2 minutes. The light body and the heavy body impression materials and the dental tray adhesive were all three cured simultaneously. The mold impression retained good integrity with the tray as it was rocked slightly and extracted from the teeth by normal hand manipulation.

The dental impression mold was found to be usable immediately for pouring up in gypsum or other suitable material. A gypsum pour-up was done with the dental impression mold still positioned tightly in position in the tray. The preparation and pouring of the gypsum was in conventional manner using the dental impression mold. The gypsum cast was removed from the mold by hand force and the mold remained stably attached to the dental tray.

The novel impression tray and method of using the same described hereinabove comprises an advantageous advance in dental technology especially in the preparation of dental restorations. As has been indicated above, one of the principal advantages of the present invention comprises the substantial saving in time to convert a flowable or viscous impression material into a permanent elastomeric mold configuration having memory and suitable for making accurate reproductions of anatomical items in the oral cavity for use in the fabrication of dental restorations. The preferred novel polymerizable impression material is preferably of a premixed nature and made available to a dental operatory or laboratory, whereby mixing of two or more ingredients is not necessary as has been required herebefore.

Effecting the conversion of the conventional flowable material into a permanent elastomeric mold requires a minimum of 8 to 10 minutes and frequently as much as 15 minutes or more, whereas with the present invention, the time for effecting polymerization of the preferred premixed impression material referred to hereinabove can be achieved in as little as 1 or 2 minutes and preferably within a maximum of 3 minutes, depending upon the strength of the visible actinic light applied to the impression material through the walls of the tray, and the size and configuration of the tray and amount of dental impression material used. The preferred actinic light which is to be employed in conjunction with the present invention is visible light within the range of 350 to 600 nanometers and this has been found to be highly effective to polymerize the starting material into an elastomeric mold form having permanent memory.

It will be clear to those skilled in the art that partial dental impression trays may be constructed according to the present invention for taking impressions of independent quadrants of the teeth forming the upper and lower dentition in the human mouth. The tray would preferably still be curved sufficiently to receive at least a partial arch-shaped group of teeth and the channel-shaped cross-section would be wider than the teeth to be received as has been illustrated.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

I claim:

1. For use with dental impression material capable of being polymerized by exposure to actinic light, a dental impression tray curved sufficient to receive at least a partial arch-shaped group of teeth and channel-shaped in cross-section and wider than the teeth to be received therein, said channel-shaped cross-section providing a recess adapted to hold a predetermined amount of said dental impression material for forming the impression of surfaces of said teeth therein, said tray comprising a substantially planar wall that forms the bottom of said channel and at least a first projecting wall projecting from one side of said bottom wall, said first projecting wall projecting from said bottom wall at an angle of about 70° to about 120°; the improvement comprising said tray being formed from substantially transparent plastic material said tray being optically shaped such that said bottom wall merges with said first projecting wall at a joint wall which has an effective outside angle of about 35° to about 55° to both said bottom wall and said first projecting wall, said joint wall predominantly transmitting actinic light and said side wall and said bottom wall capable of both substantial passing and substantial transmitting of actinic light, whereby light within the walls is retained against undesirable exit at the junctures while the admittance of new light is at all times facilitated.

2. The dental impression tray according to claim 1 wherein said tray comprising a plastic that transmits at least 50% of the actinic light comprises at least two different wave lengths between 350 and 600 nanometers that are spaced at least 10 nanometers apart.

3. The impression tray according to claim 2 in which said plastic transmits at least 70% of said light.

4. The impression tray according to claim 3 comprising a second projecting wall project from the opposite side of said bottom wall from said first projecting wall at an angle of about 70° to about 120° said bottom wall merging with each respective first and second side walls at a respective joint wall, said first and said second joint walls having respective effective outside angles of about 35° to about 55°.

5. The dental impression tray according to claim 4 comprising acrylic and wherein said tray comprising a plastic that transmits at least 80% of the light of at least two different wave lengths within the visible actinic light spectrum of 350 and 600 nanometers that are spaced at least 10 nanometers apart and said first and second projecting walls project from the opposite side of said bottom wall at an angle of about 85° to about 95°, and said first and said second joint walls having respective effective outside angles of about 43° to about 47°.

6. The dental impression tray of claim 1 in which said walls are substantially planar and are adapted to permit easy movement of a light against or adjacent to said walls on the outside of said tray.

7. The dental impression tray of claim 6 in which the relative shape and position of said walls is adapted to pipe light introduced therein around an internal U channel in said tray formed by the relative positions of said walls.

8. The dental impression tray of claim 1 in which said joint wall acts as a beam splitter when said light source is adjacent thereto, causing light from said light source to enter into impression material to the left and to the right of said joint wall.

9. The dental impression tray of claim 1 which further comprises a rear wall in said bottom wall, said rear wall being at the end of said arch and having a 45° angle with respect to said bottom wall, wherein said rear wall acts as a prism which guides light exiting from the impression material at the end of the arch back into said impression material.

* * * * *